United States Patent [19]

Weiss et al.

[11] 3,944,663

[45] Mar. 16, 1976

[54] MILD LIGHT DUTY DETERGENT CONTAINING HOMOPOLYMERS OF ETHYLENE OXIDE

[75] Inventors: Sidney Weiss, Levittown, Pa.; Victor Temnikow, Irvington; Edward Eigen, East Brunswick, both of N.J.

[73] Assignee: Colgate Palmolive Company, New York, N.Y.

[22] Filed: July 9, 1973

[21] Appl. No.: 377,866

Related U.S. Application Data

[63] Continuation of Ser. No. 153,792, June 16, 1971, abandoned.

[52] U.S. Cl................... 424/78; 252/89 R; 252/153; 252/173; 252/548; 252/550; 252/551; 252/554; 252/555; 252/558; 252/DIG. 2; 252/DIG. 5; 252/DIG. 14

[51] Int. Cl.$^2$.. A61K 7/40; A61K 7/50; C11D 3/20; C11D 3/48

[58] Field of Search ............. 252/89, 106, 109, 122, 252/132, 121, 531, 173, 535, 539, 540, 554, 558, 559, DIG. 2, DIG. 3, DIG. 5, DIG. 13, DIG. 14; 260/2 A, 615 B; 424/170, 78

[56] References Cited

UNITED STATES PATENTS

| | | | |
|---|---|---|---|
| 2,999,068 | 9/1961 | Pilcher | 252/528 |
| 3,248,333 | 4/1966 | O'Roark | 252/144 |
| 3,332,876 | 7/1967 | Walker | 252/541 |
| 3,513,099 | 5/1970 | Hans | 252/541 |

OTHER PUBLICATIONS

Harding et al.: 10, "Ethylene Oxide Polymers", Technical Center, Union Carbide Corp., South Charleston, West Va., pp. 191–196.

Davidson et al.: Water Soluble Resins, Chapt. 9, "Ethylene Oxide Polymers" by Berger et al., Union Carbide Chem. Co., N.Y. pp. 169–171 & 192–198.

*Primary Examiner*—Dennis L. Albrecht

*Attorney, Agent, or Firm*—Richard N. Miller; Kenneth A. Koch; Herbert Sylvester

[57] ABSTRACT

Mild light duty detergent formulation including an anionic surfactant having skin irritating characteristics and an effective amount of a homopolymer of ethylene oxide to reduce said skin irritation.

4 Claims, No Drawings

MILD LIGHT DUTY DETERGENT CONTAINING HOMOPOLYMERS OF ETHYLENE OXIDE

This is a continuation of Ser. No. 153,792, filed June 16, 1971, now abandoned.

This invention relates to cleaning and washing formulations that, as a matter of course, come into substantial and prolonged contact with the user's hands. More specifically, the invention provides exceptionally mild detergent formulations of the type typically used for the manual washing of dishes, the hand washing of delicate fabrics, etc. Formulations of this type are commonly known as light duty detergents and can be in either dry powder or liquid form.

Since detergent formulations of this type come into substantial contact with the user's hands, they should, most advantageously, be formulated to impart a minimum amount of irritation to human skin. Although the amount of irritation imparted to an individual's hands by a particular detergent formulation is subjective, varying from person to person, it is well known that certain detergent ingredients, particularly anionic surfactants, cause some degree of skin irritation to virtually all individuals. This irritation is usually manifested by the reddening or chapping of the affected area or in extreme cases, actual cracking of the skin.

Since the most commonly used detergent formulations of this type are manual dishwashing liquids, the present invention will be described primarily with reference to those products. However, as will soon be apparent, the principles of the invention can also be advantageously used with dry powder detergent products and even detergent and soap-detergent toilet bars of the type that have objectionable skin irritating characteristics.

Although mildness to the skin is a very important consideration in formulating light duty detergents, other factors, such as grease cutting ability, billowing and consistant suds and, detergency properties are also quite important. These latter characteristics e.g. grease cutting, billowing consistent suds and detergency, are best obtained by a formulation comprising an aqueous solution of an anionic surface active agent in combination with various auxiliary ingredients that provide specific desired properties. The resulting formulation should be easy and economical to use, produce billowing and stable suds in the presence of fats and grease, have an attractive color and odor, and should be mild to the user's hands. The present invention provides an auxiliary ingredient for light duty detergent formulations that substantially reduces the irritation and chapping etc. usually experienced when using formulations of this type.

In accordance with the invention, from about 0.01 to about 5.0 percent by weight of a high molecular weight homopolymer of ethylene oxide is incorporated into light duty detergents to substantially reduce the skin irritation that may normally be caused by these products. The polymeric additive of the invention is in the form of a white granulated water soluble solid. It is suitable for use in aqueous liquid formulations and can be easily dry mixed with powdered formulations and detergent or soap-detergent bars. The polymeric additive of the invention is a homopolymer of ethylene oxide of the formula $(CH_2—CH_2—O)_n$ wherein *n* is an integer having a value as high as about $1.5 \times 10^5$ e.g. a molecular weight of as much as 8,600,000. Preferably, the polymeric additive used in accordance with the invention has a molecular weight between about $1 \times 10^5$ and $4 \times 10^6$.

In further accordance with the invention, the amount of polymeric additive incorporated into the new formulation is inversely related to the molecular weight of the polymer. For example, an equivalent reduction in the skin irritation level caused by a given liquid dishwashing detergent can be obtained by incorporating therein about 0.1 percent by weight of the polymeric material having a molecular weight of about $4 \times 10^6$ as with 0.5 percent by weight the same polymeric material having a molecular weight of about $6 \times 10^5$. In both cases, a substantial reduction in the amount of skin irritation caused by the formulation is obtained without any significant adverse effects on the other desirable properties of the formulation.

The new polyether additives are prepared in the presence of a catalyst and an organic diluent in which the ethylene oxide monomer is soluble and the polymeric product is insoluble. During polymerization the polymer chain grows through the addition of ethylene oxide monomer to an alkoxide radical derived from previously reacted monomer units. Ethylene oxide homopolymer derivatives prepared by this suspension polymerization technique are white, granular, water soluble materials ranging in molecular weight from about 100,000 to eight million and more. The polymer has been determined to be largely a linear chain with sufficient mobility under most conditions to form large crystalline aggregates. These polyether resins differ primarily in molecular weight and are very similar in chemical structure and physical properties. Typical physical properties are as follows:

| | |
|---|---|
| Melting Point | 65±2°C |
| Specific Gravity | 1.21 g./cu.cm. |
| Bulk Density | 17 to 33lb./cu |
| Moisture Content, as supplied | 1% |
| Ash Content, as CaO | 0.3 to 0.8% |
| Heat of Fusion | 33 cal./g. |
| Particle Size | 98% through 10 mesh |

Liquid light duty detergents generally comprise, in aqueous solution, a primary active ingredient, a modifying or secondary active ingredient, solubilizing agents and other minor components. The combination of primary and secondary active ingredients usually comprises about 15 to about 40 percent by weight of the formulation with the primary active ingredient usually making up 10 to 35 percent by weight.

The primary active ingredient is usually an anionic surface active agent although nonionic and cationic surfactants can be used. The most commonly used anionic surfactants are the linear alkyl benzene sulfonates having a $C_8$ to $C_{18}$ alkyl chain. Most preferred of this group are the sodium and ammonium salts of dodecylbenzene sulfonate. Ethoxylated sulfated fatty alcohols, usually in the form of a sodium or ammonium salt, and various combinations of this class of surfactant with alkyl benzene sulfonates are also frequently used as the primary active ingredient in liquid dishwashing detergents. Olefin sulfonates and paraffin sulfonates can also be used as the primary active ingredient in formulations of this type. In dry powder light duty formulations for the laundering of fine fabrics, the primary active ingredient is usually an alkylbenzene sulfonate or a sulfated ethoxylated of alkyl phenol such as octylphenol and nonylphenol, generally as the ammonium salt.

Representative olefin sulfonates include long chain hydroxyalkane sulfonate or mixtures of alkenesulfonates and hydroxyalkanesulfonates. These olefin sulfonate detergents may be prepared, in known manner, by the reaction of $SO_3$ with long chain olefins (of 8–25, preferably 12–21, carbon atoms) of the formula $RCH{=}CHR_1$, where R is alkyl and $R_1$ is alkyl or hydrogen, to produce a mixture of sultones and alkenesulfonic acids, which mixture is then treated to convert the sultones to sulfonates. Examples of paraffin sulfonates are those having about 10–20, preferably about 15–20, carbon atoms such as the primary paraffin sulfonates made by reacting long chain alpha olefins and bisulfites (e.g. sodium bisulfite) or paraffin sulfonates having the sulfonate groups distributed along the paraffin chain such as the products made by reacting a long chain paraffin with sulfur dioxide and oxygen under ultra-violet light followed by neutralization with NaOH or other suitable base (as in U.S. Pat. Nos. 2,503,280; 2,507,088; 3,260,741; 3,372,188 and German Pat. No. 735,096).

Liquid dishwashing detergents almost invariably also include as much as 25 percent, typically about 5–15 percent by weight, of a secondary active ingredient in addition to the primary active ingredient. Although the typically used primary active ingredients usually provide a profusion of suds in clear water, the suds are substantially depleted when fat or grease is present in the water which, of course, is quite common. The function of the secondary active ingredient is primarily to maintain the volume and stability of suds during the dishwashing operation. Additionally, and most advantageously, the secondary active ingredient can also provide added detergency to the light duty formulation.

The most effective secondary active ingredients are the water soluble fatty alkylolamides, such as lauric and myristic mono and di ethanolamides. A combination of two or more of these fatty alkylolamides are usually incorporated into liquid dishwashing formulations.

The solubilizing agents usually employed in liquid light duty detergents are present in amounts of from about 5 percent to about 15 percent by weight. These include the water soluble lower alkyl alcohols, e.g. methanol, ethanol, isopropanol, polyethylene glycol and hydrotropes such as sodium xylene sulfonate. The presence of sodium xylene sulfonate is particularly advantageous in increasing the water solubility of the sodium salts of the alkyl benzene sulfonates. Other minor components of liquid dishwashing detergents include various perfumes and colorants such as opacifying agents and fluorescent dyes.

The following specific examples are further illustrative of the invention but it is understood that the invention is not limited thereto. Detergent formulations are prepared in the usual manner and all amounts and proportions are by weight unless otherwise indicated.

EXAMPLE 1

A liquid light duty detergent suitable for manual dishwashing and having the following composition is formulated:

| Ingredients | Parts |
|---|---|
| Water | 46.3 |
| Ethanol | 5.8 |
| Sodium xylene sulfonate | 4.0 |
| Ammonium $C_{12}$–$C_{15}$ alkyl triethenoxy ether sulfate | 13.0 |
| Linear dodecyl benzene sulfonate (sodium salt) | 23.0 |
| lauric/myristic monoethanolamide | 5 |
| Perfume and colorants | 2.8 |
| Ethylene oxide homopolymer (M.W. $4 \times 10^6$) | 0.1 |

The foregoing formulation, when panel tested by housewives in comparison to the same formulation without the polyether additive, showed a substantial decrease in the amount and severity of skin irritation experienced.

EXAMPLE 2

The formulation of example 1 is repeated with 0.5 parts of an ethylene oxide homopolymer having a molecular weight of $6 \times 10^5$ in place of the polyether additive of example 1. Similar panel test results showed the same approximate decrease in the severity of irritation experienced relative to the same formulation without the polyether additive.

EXAMPLE 3

Example 2 is repeated except that 0.1 parts of the polyether additive are incorporated into the formulation instead of 0.5 parts. Although the panel test results for this formulation were not as dramatic as those for the formulations of examples 1 or 2, a substantial reduction in the amount of skin irritation experienced relative to the same formulation without the polyether component, was noted.

EXAMPLE 4

Example 1 is repeated with 5.0 parts of an ethylene oxide homopolymer having a molecular weight of $1 \times 10^5$ in place of the polyether used in example 1. Similar panel test results showed a substantial decrease in the severity of skin irritation experienced, relative to the same formulation without the polyether additive.

EXAMPLE 5

A liquid light duty detergent suitable for manual dishwashing and having the following composition is formulated:

| Ingredients | Parts |
|---|---|
| Water | 45 |
| Ethoxylated sulfated $C_{12}$–$C_{15}$ (ammonium salt) | 10 |
| alpha Olefin Sulfonates ($C_{12}$–$C_{21}$) | 18 |
| Lauric/myristic diethanolamide | 5 |
| Ethanol | 10 |
| Perfume and colorants | 0.5 |
| Ethylene oxide homopolymer (M.W. $6 \times 10^5$) | 0.25 |

The amount and severity of skin irritation experienced when using this formulation for the manual washing of dishes is significantly reduced by the presence of the ethylene oxide homopolymer component.

EXAMPLE 6

A liquid light duty detergent, suitable for washing fine fabrics by hand and having the following composition, can be formulated:

| Ingredients | Parts |
|---|---|
| Water | 51.1 |
| Sulfated octylphenol-ethylene oxide condensate (ammonium salt) | 28.6 |
| Lauric diethanolamide | 10.4 |
| isopropanol | 6.3 |
| Perfume and colorants | 3.1 |
| Ethylene oxide homopolymer (M.W. $3\times10^5$) | 0.5 |

The degree of skin irritation imparted by this formulation is significantly reduced by the presence of the polyether component.

EXAMPLE 7

A dry granular detergent powder having the following composition can be formulated by the usual techniques.

| Ingredients | Parts |
|---|---|
| lauryl sulfate (sodium salt) | 40.0 |
| sodium sulfate | 57.8 |
| moisture | 1.7 |
| Ethylene oxide homopolymer (M.W. $6\times10^5$) | 0.5 |

The severity of skin irritation caused by this formulation in wash water is significantly reduced by the presence of the polyether component.

Similarly, and in accordance with the invention, the new polyether additive can be incorporated into many different and varied detergent formulations that normally exhibit a relatively high or unacceptable level of skin irritation. This would include liquid and dry powder cleaning agents that are formulated for various purposes and to which the user's skin is exposed to for a substantial period of time as well as to the specific formulations disclosed therein. Incorporation of the polyether additive of the invention into detergent or soap and detergent toilet bars in order to provide a milder bar of this type can also be accomplished in accordance with the invention.

Although the foregoing specific examples include preferred and typical formulations, they should not be taken as limitations on the invention. Accordingly, reference should be made to the following claims in determining the full scope of the invention.

We claim:

1. A method for substantially reducing skin irritation of the hands by a light duty liquid or powder detergent formulation consisting essentially of 10% to 35% by weight of a water-soluble anionic surfactant having skin irritating characteristics and selected from the group consisting of $C_8$–$C_{18}$ aklyl benzene sulfonates, $C_8$–$C_{18}$ alkyl sulfates containing from 0 to 3 ethenoxy groups in the molecule, $C_8$–$C_{25}$ olefin sulfonates, $C_{10}$–$C_{20}$ paraffin sulfonates, $C_8$–$C_9$ alkyl phenol ethoxamer sulfates, and mixtures thereof which comprises contacting the hands with an aqueous washing solution of said detergent formulation containing said skin-irritating detergent and an effective amount of a homopolymer of ethylene oxide having the general formula $(CH_2CH_2\mathbf{0})n$ wherein n is an integer sufficient to provide a molecular weight between about $1 \times 105$ and $4 \times 10^6$, said polymer being from about 0.01 to about 5% by weight of said formulation, with the balance of said formulation being either sodium sulfate or an aqueous medium containing up to 15% by weight of a solubilizing agent selected from the group consisting of $C_2$–$C_3$ alkanols, polyethylene glycols and sodium xylene sulfonate.

2. The method of claim 1 further characterized by including from about 0.1 to about 0.5 percent by weight of said homopolymer having a molecular weight between $4\times10^6$ and $6\times10^5$.

3. The method of claim 1 wherein said anionic surfactant is chosen from the group consisting of sodium and ammonium salts of linear dodecylbenzene sulfonate.

4. A method in accordance with claim 1 wherein said formulation further includes from about 5% to 25% by weight of a $C_{12}$–$C_{14}$ fatty acid ethanolamide.

* * * * *